United States Patent

Toth et al.

[11] 4,024,269
[45] May 17, 1977

[54] BENZIMIDAZOLE DERIVATIVES AND FUNGICIDAL COMPOSITION AND METHOD

[75] Inventors: Geza Toth; Istvan Toth, both of Budapest, Hungary

[73] Assignee: Chinoin Gyogyszer es Vegyeszeti Termekek Gyara Rt., Budapest, Hungary

[22] Filed: June 16, 1976

[21] Appl. No.: 696,764

Related U.S. Application Data

[63] Continuation-in-part of Ser. No. 571,763, April 25, 1975, Pat. No. 3,978,075.

[30] Foreign Application Priority Data

May 2, 1974   Hungary ................................. 1473

[52] U.S. Cl. .............................. 424/273; 260/309.2
[51] Int. Cl.² ......................................... C07D 405/12
[58] Field of Search ................. 260/309.2; 424/273

[56] References Cited

OTHER PUBLICATIONS

Osieka et al., Chem. Abst. 1973, vol. 79, No. 137151a.

Nenitzescu et al., Chem. Abst. 1958, vol. 52, Columns 11810–11811.

*Primary Examiner*—Natalie Trousof
*Attorney, Agent, or Firm*—Karl F. Ross; Herbert Dubno

[57] ABSTRACT

A fungicidal and fungistatic composition contains, as an effective ingredient, a compound of the formula

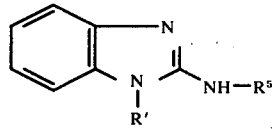

and antifungal and pharmaceutically effective salts thereof wherein $R^1$ is H and $R^5$ is a group with the formula

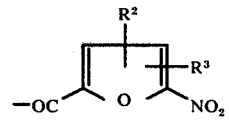

in which $R^2$ and $R^3$ are each hydrogen or $C_1$–$C_6$ alkyl.

4 Claims, No Drawings

BENZIMIDAZOLE DERIVATIVES AND FUNGICIDAL COMPOSITION AND METHOD

This application is a continuation-in-part of application Ser. No. 571,763 filed 25 Apr. 1975, now U.S. Pat. No. 3,978,075.

This invention relates to new benzimidazole derivatives, and the salts thereof, and the use of the same.

According to the present invention, there are provided compounds of the formula I

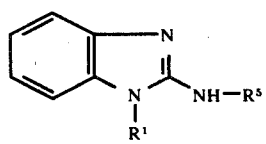

and salts thereof, wherein
$R^1$ is hydrogen, and $R^5$ is a group of the formula II

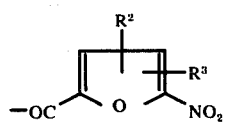

The term "alkyl group" as used herein means straight or branched chained saturated aliphatic hydrocarbon groups, having 1–6 carbon atoms, e.g. methyl, ethyl, n-propyl, isobutyl, etc. The term "aryl group" is used herein to refer to aromatic groups, having 7–10 carbon atoms, e.g. phenyl or naphthyl, which may be substituted by one or more substituents selected from the group consisting of halogen, alkyl, and alkoxy. Preferred substituted aryl groups are the 3-chlorophenyl and 3,4-dichlorophenyl groups. The term "cycloalkyl group" is used herein to identify cycloalkyl groups having 3–6 carbon atoms preferably cyclopropyl, cyclobutyl, cyclopentyl and cyclohexyl. The term alkoxy means $C_1$ to $C_6$ straight or branched alkoxy. Halogen means fluoro, chloro, bromo or rodo.

The salts of the compounds of the formula I may be formed with inorganic or organic acids, e.g. hydrochlorides, hydrobromides, sulphates, acetates, formiates, lactates, tartarates, etc. The salts to be used in therapy must be formed with pharmaceutically acceptable acids.

A particularly preferred derivative of the formula I is the following compound:
N-(2'-benzimidazolyl)-5-nitro-2-furane-carboxylic acid amide.

According to a further feature of the present invention, there is provided a process for the preparation of compounds of the formula I and salts thereof, wherein $R^1$ and $R^5$ have the same meaning as stated above, which comprises
reacting a compound of the formula IV

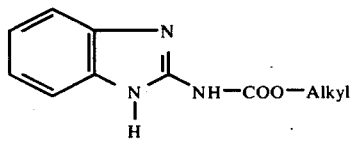

or V

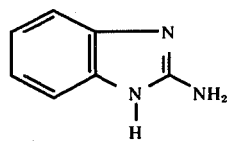

with a reactive acid derivative containing a group of the formula II.

According to a preferred embodiment of the process a compound of the formula IV or V is reacted with 5-nitro-2-furoyl-carboxylic acid, or with a halide or ester thereof preferably with 5-nitro-2-furoyl-carboxylic acid-chloride.

The process is carried out preferably in an organic solvent in the presence of a basic substance. If a carboxylic acid ester is used, it is preferred to remove the alcohol formed continuously. If the reaction is carried out by using the free acid it is preferable to carry out the reaction in the presence of a condensing agent (e.g. dicyclohexyl-carbodiimide) in dimethylformamide.

The compounds of the formula I may be converted into their salts in a conventional manner preferably by reacting the compound of the formula I with an approximately equimolar amount of the acid in the presence of an organic solvent.

The compounds of the formula I, and their salts possess valuable fungicidal properties and may be used in human and veterinary therapy as well as in agriculture.

According to a further feature of the present invention there are provided pharmaceutical compositions for use in both human and veterinary therapy comprising at least one compound of the formula I or a salt thereof in admixture with suitable pharmaceutically acceptable solid or liquid carriers or diluents.

The pharmaceutical compositions may be finished in the form of solutions, suspensions, emulsions, tablets, dragees, powder mixtures, ointments or granules. The compositions contain conventional carriers used in pharmacy (e.g. starch, talc, calcium, carbonate, magnesium stearate, water, polyalkylene glycols, etc.)

According to a still further feature of the present invention, there are provided disinfectants, comprising at least one compound of the formula I, or salts thereof. The said disinfectants are preferably formulated in the form of aqueous solutions. Such aqueous solutions containing about 1% of a compound of the formula I or a salt thereof are particularly suitable for the disinfecting of swimming pools, or other large objects subject to fungal infections.

According to a further feature of the present invention, there are provided pesticidal compositions, comprising at least one compound of the formula I, or a salt thereof in admixture with suitable inert, solid or liquid carriers or diluents.

The said pesticides may be finished as dusting powders, sprays, granules, emulsifiable concentrates, etc. The compositions contain carriers and diluents generally used in the formulation of pesticides. The composition may also contain surface active agents or other additives.

The pesticides contain from about 0.001% to about 95% of the active ingredient of the formula I. While the diluted compositions suitable for direct use may contain generally from about 0.001 to about 1% of the active ingredient, the concentrates may contain from about 20% to about 80% of active ingredients.

The pesticidal compositions of the present invention exhibit particularly strong activity against fungi belonging to the Fusarium. Basidiomycetes or Helminthosporium family. The compositions are particularly effective with wheat plants against *Tillethia tritici*, with rye plants against *Fusarium nivale*, and with sugar beet plants against *Cercospore beticola*. The compositions may be advantageously used for seed dressing.

According to a further feature of the present invention, there are provided cosmetic compositions comprising as active ingredient at least one compound of the formula I, or a salt thereof.

Further details of the present invention are to be found in the Examples.

EXAMPLE 13.3 g. (0.1 mole) of 2-amino-benzimidazole are suspended in 250 ml. of dioxane, whereupon 10 g. of triethylamine are added. The mixture is heated to 60° C, whereupon at this temperature 17.5 g. (0.1 mole) of 5-nitro-2-furane-carbonyl chloride are added. The reaction mixture is stirred at 60° C for 2 hours, whereupon it is cooled to 15° C. Thus. 25.5 g. of N-(2'-benzimidazolyl)-5-nitrofurane carboxylic acid amide are obtained. Mp.: 240°–242° C.

We claim:
1. A compound of the formula

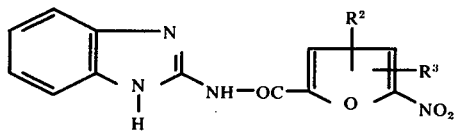

and the antifungal and pharmaceutically effective salts thereof wherein $R^2$ and $R^3$ are each hydrogen or $C_1$–$C_6$ alkyl.

2. The compound defined in claim 1 which consists of N-(2' benzimidazolyl)-5-nitro-2 furane carboxylic acid amide.

3. A fungicidally effective composition consisting essentially of 0.001 to 95% of the compound of claim 1 in a carrier.

4. A method of protecting plants against fungi comprising applying to the plants an effective amount of the compound defined in claim 1.

* * * * *